(12) United States Patent
Giorgetti

(10) Patent No.: US 10,857,116 B2
(45) Date of Patent: Dec. 8, 2020

(54) COMPOSITIONS FOR TREATMENT OF PAIN IN PATIENTS WHO UNDERWENT ELECTIVE ANTHROPLASTY

(71) Applicant: Professional Dietetics International S.r.l., Milan (IT)

(72) Inventor: Paolo Luca Maria Giorgetti, Milan (IT)

(73) Assignee: Professional Dietetics International S.r.l., Milan (IT)

( * ) Notice: Subject to any disclaimer, the term of this patent is extended or adjusted under 35 U.S.C. 154(b) by 0 days.

(21) Appl. No.: 15/760,281

(22) PCT Filed: Sep. 8, 2016

(86) PCT No.: PCT/IB2016/055354
§ 371 (c)(1),
(2) Date: Mar. 15, 2018

(87) PCT Pub. No.: WO2017/051272
PCT Pub. Date: Mar. 30, 2017

(65) Prior Publication Data
US 2019/0046485 A1 Feb. 14, 2019

(30) Foreign Application Priority Data

Sep. 24, 2015 (IT) .................... 102015000055027

(51) Int. Cl.
| | | |
|---|---|---|
| *A61K 31/198* | (2006.01) | |
| *A61P 29/00* | (2006.01) | |
| *A61K 31/405* | (2006.01) | |
| *A61K 31/4172* | (2006.01) | |

(52) U.S. Cl.
CPC .......... *A61K 31/198* (2013.01); *A61K 31/405* (2013.01); *A61K 31/4172* (2013.01); *A61P 29/00* (2018.01)

(58) Field of Classification Search
CPC ................ A61K 31/198; A61K 31/405; A61K 31/4172; A61P 29/00
See application file for complete search history.

(56) References Cited

U.S. PATENT DOCUMENTS

| 5,053,429 A | 10/1991 | Hirsch et al. |
|---|---|---|
| 9,615,575 B2 | 4/2017 | Dioguardi |
| 2014/0371289 A1* | 12/2014 | Dioguardi ............. A01N 37/44 514/423 |
| 2017/0027985 A1* | 2/2017 | Gingrich ................ A23L 33/15 |
| 2017/0143025 A1* | 5/2017 | Rason .................... A61K 45/06 |

FOREIGN PATENT DOCUMENTS

| BE | 896 753 | 9/1983 | |
|---|---|---|---|
| CN | 104222137 A | 12/2014 | |
| EP | 0 004 040 | 9/1979 | |
| WO | WO 98/08520 | 3/1998 | |
| WO | WO 00/50028 | 8/2000 | |
| WO | WO 03/005997 | 1/2003 | |
| WO | WO-2011043647 A1 * | 4/2011 | ........... A61K 9/1617 |

OTHER PUBLICATIONS

International Search Report and Written Opinion of the ISA for PCT/IB2016/055354 dated Dec. 8, 2016, 13 pages.
[Online] Gray, "Amino acid supplements may speed up knee-replacement recovery", NUTRAingredients.com, Oct. 28, 2013, p. 3pp.
Dreyer et al., "Essential amino acid supplementation in patients following total knee arthroplasty", Journal of Clinical Investigation, vol. 123, No. 11, Nov. 2013, pp. 4654-4666.
Hiroyuki et al., "Leucine-enriched essential amino acids attenuate muscle soreness and improve muscle protein synthesis after eccentric contractions in rats", Amino Acids, vol. 47, No. 6, Jun. 2015, pp. 1193-1201.
Richards et al., "Comparison of the Efficacy and Safety of Dual-Opioid Treatment with Morphine Plus Oxycodone Versus Oxycodone/Acetaminophen for Moderate to Severe Acute Pain After Total Knee Anthroplasty", Clinical Therapeutics, vol. 35, No. 4, Apr. 2013, pp. 498-511.
Russia Search Report dated Jan. 15, 2020, issued in Russian Patent Application No. 2018113332, with English translation of extract of references table, 3 pages.
Russia Office Action dated Jan. 17, 2020, issued in Russian Patent Application No. 2018113332, 7 pages.
Affas, Fatin, et al., "Pain control after total knee arthroplasty: a randomized trial comparing local infiltration anesthesia and continuous femoral block," Acta Orthopaedica 2011, vol. 82, No. 3, pp. 441-447.
Dreyer, Hans C., et al., "Essential amino acid supplementation in patients following total knee arthroplasty," The Journal of Clinical Investigation, vol. 123, No. 11, Nov. 2013, pp. 4654-4666.
Hou, Huimin, et al., "Application Technology of Pharmaceutical Excipients," 2nd Edition, China Medical Science and Technology Press, Jul. 2002, 4 pages.
Patent Search Report dated Mar. 25, 2020, issued in Chinese Application No. 2016800560994, 2 pages.

* cited by examiner

*Primary Examiner* — Sarah Pihonak
*Assistant Examiner* — Jason Deck
(74) *Attorney, Agent, or Firm* — Nixon & Vanderhye P.C.

(57) ABSTRACT

Amino acids compositions for use in the treatment of pain in patients who underwent elective arthroplasty.

12 Claims, 2 Drawing Sheets

Harris Hip Score

Hip ID:
Study Hip: ☐ Left  ☐ Right
Examination Date (MM/DD/YY): / /
Subject Initials:
Medical Record Number:

Interval:

Harris Hip Score

Pain *(check one)*
- ☐ None or ignores it (44)
- ☐ Slight, occasional, no compromise in activities (40)
- ☐ Mild pain, no effect on average activities, rarely moderate pain with unusual activity; may take aspirin (30)
- ☐ Moderate Pain, tolerable but makes concession to pain. Some limitation of ordinary activity or work. May require Occasional pain medication stronger than aspirin (20)
- ☐ Marked pain, serious limitation of activities (10)
- ☐ Totally disabled, crippled, pain in bed, bedridden (0)

Limp
- ☐ None (11)
- ☐ Slight (8)
- ☐ Moderate (5)
- ☐ Severe (0)

Support
- ☐ None (11)
- ☐ Cane for long walks (7)
- ☐ Cane most of time (5)
- ☐ One crutch (3)
- ☐ Two canes (2)
- ☐ Two crutches or not able to walk (0)

Distance Walked
- ☐ Unlimited (11)
- ☐ Six blocks (8)
- ☐ Two or three blocks (5)
- ☐ Indoors only (2)
- ☐ Bed and chair only (0)

Sitting
- ☐ Comfortably in ordinary chair for one hour (5)
- ☐ On a high chair for 30 minutes (3)
- ☐ Unable to sit comfortably in any chair (0)

Enter public transportation
- ☐ Yes (1)
- ☐ No (0)

Stairs
- ☐ Normally without using a railing (4)
- ☐ Normally using a railing (2)
- ☐ In any manner (1)
- ☐ Unable to do stairs (0)

Put on Shoes and Socks
- ☐ With ease (4)
- ☐ With difficulty (2)
- ☐ Unable (0)

Absence of Deformity (All yes = 4; Less than 4 =0)
- Less than 30° fixed flexion contracture ☐ Yes ☐ No
- Less than 10° fixed abduction ☐ Yes ☐ No
- Less than 10° fixed internal rotation in extension ☐ Yes ☐ No
- Limb length discrepancy less than 3.2 cm ☐ Yes ☐ No

Range of Motion *(*indicates normal)*
- Flexion (*140°) _____
- Abduction (*40°) _____
- Adduction (*40°) _____
- External Rotation (*40°) _____
- Internal Rotation (*40°) _____

Range of Motion Scale
- 211° - 300° (5)        61° - 100 (2)
- 161° - 210° (4)        31° - 60° (1)
- 101° - 160° (3)        0° - 30° (0)

Range of Motion Score _____

Total Harris Hip Score _____

Figure 2

COMPOSITIONS FOR TREATMENT OF PAIN IN PATIENTS WHO UNDERWENT ELECTIVE ANTHROPLASTY

This application is the U.S. national phase of International Application No. PCT/IB2016/055354 filed Sep. 8, 2016 which designated the U.S. and claims priority to IT Patent Application No. 102015000055027 filed Sep. 24, 2015, the entire contents of each of which are hereby incorporated by reference.

FIELD OF THE INVENTION

The present invention concerns compositions useful in the treatment of pain in patients who underwent elective arthroplasty, preferably during rehabilitation.

BACKGROUND OF THE INVENTION

Elective hip arthroplasty (EHA) is a surgical technique used for patients with damaged hip joints after degenerative osteoarthritis or an injury. One and half million EHA are carried out all over the world each year. In Italy, there are about 100,000 annual EHA operations at a cost of approximately 1.3 billion euros, of which 500 million euros should be added for subsequent rehabilitation treatment. The total economic burden of EHA plus rehabilitation is 1.6% of national annual budget for the health care system.

EHA and Post-EHA rehabilitation allows patients to regain physical ability and improve their quality of life. However, a number of factors may hinder both duration and outcome of rehabilitation, including preoperative functional state, postoperative pain, and infection. Specifically, persistence of pain can lengthen functional restoration time, reduce clinical outcome and increase the need for additional rehabilitation.

Limiting these post-surgery alterations could accelerate and enhance the retrieval of operated hip-joint dysfunction.

There is therefore the need of new compositions which may enhance the recovery of patients undergoing elective arthroplasty.

OBJECT AND SUMMARY OF THE INVENTION

The object of the present invention is to provide new compositions which may enhance the recovery of patients undergoing elective arthroplasty by reducing and/or eliminating pain, preferably during rehabilitation.

According to the invention, the above object is achieved thanks to the method specified in the ensuing claims, which are understood as forming an integral part of the present description.

In an embodiment, the instant disclosure discloses an amino acid composition for use in the treatment of pain in patients who underwent elective arthroplasty comprising at least a first active agent, wherein the first active agent comprises the aminoacids leucine, isoleucine, valine, lysine, threonine, histidine, phenylalanine, methionine, tryptophan, tyrosine, cystine.

In a further embodiment, the instant disclosure discloses an amino acid composition for use in the treatment of pain in patients who underwent elective arthroplasty comprising at least a first and a second active agent, wherein the first active agent comprises the aminoacids leucine, isoleucine, valine, lysine, threonine, histidine, phenylalanine, methionine, tryptophan, tyrosine, and cystine, and the second active agent comprises the aminoacids glutamine, glycine and serine.

The data disclosed in the present description show that administration of amino acid compositions as disclosed herein is able to treat pain in patients who underwent elective arthroplasty thus increasing their recovery.

BRIEF DESCRIPTION OF THE DRAWINGS

The invention will now be described, by way of example only, with reference to the enclosed figures, wherein:

FIG. 2 shows the relative scores of the domains contributing to the determination of Harris Hip Score.

DETAILED DESCRIPTION OF THE INVENTION

Figure 1:
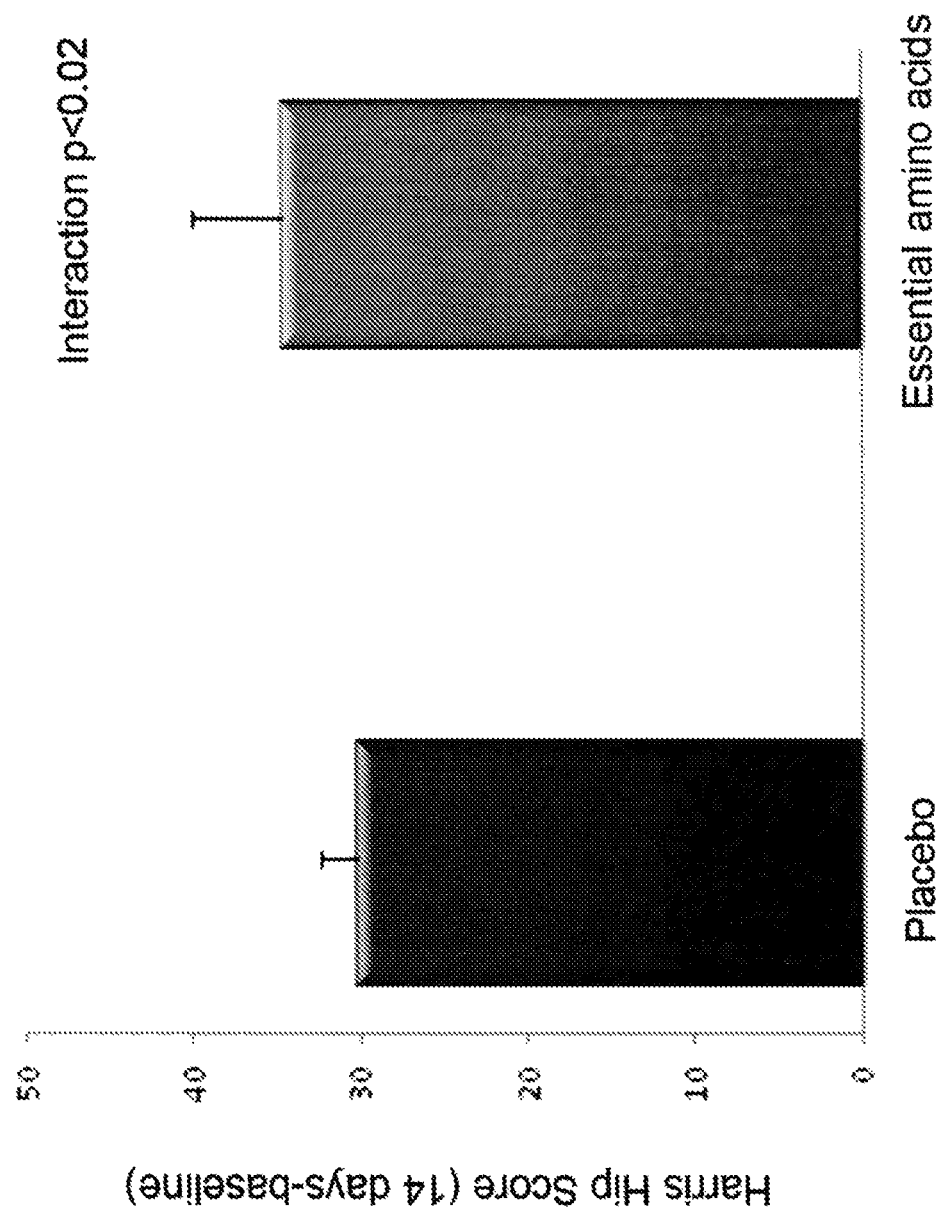
FIG. 1 shows the values of Harris Hip Score for the placebo and EAA treated groups.

The invention will now be described in detail, by way of non limiting example, with reference to patients who underwent elective hip arthroplasty.

It is clear that the scope of this description is in no way limited to elective hip arthroplasty only; patients undergoing to other elective arthroplasty, like for example knee or shoulder joint, may get beneficial effect in terms of pain treatment from the administration of the amino acid composition disclosed in the present description.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

According to an embodiment of the instant description, the amino acid composition for use in the treatment of pain in patients who underwent elective arthroplasty comprises at least a first active agent, wherein the first active agent comprises the aminoacids leucine, isoleucine, valine, lysine, threonine, histidine, phenylalanine, methionine, tryptophan, tyrosine, cystine.

According to a further embodiment of the instant description, the amino acid composition for use in the treatment of pain in patients who underwent elective arthroplasty comprises at least a first and a second active agent, wherein the first active agent comprises the aminoacids leucine, isoleucine, valine, lysine, threonine, histidine, phenylalanine, methionine, tryptophan, tyrosine, and cystine, and the second active agent comprises the aminoacids glutamine, glycine and serine.

According to a preferred embodiment of the instant description, the amino acid compositions herein disclosed are for use in the treatment of pain in patients who underwent elective hip arthroplasty.

Further specifications, in terms of amounts and ratios among the various amino acids provided for by the compositions for use in the treatment of pain in patients who underwent elective arthroplasty are contained in the attached claims, which form an integral part of the technical teaching provided herein in relation to the invention.

According to a further embodiment, the amino acid composition may comprise pharmaceutically acceptable excipients, like for example proteins, vitamins, carbohydrates, natural and artificial sweeteners and/or flavoring substances. In a preferred embodiment, the pharmaceutically acceptable excipients may be selected from whey proteins, maltodextrins, fructose, calcium caseinate, fish oil, citric acid or salts thereof, sucralose, sucrose esters, vitamin D3, group B vitamins.

The present study shows that in the rehabilitation phase of elective hip arthroplasty the patients may be associated with pain, which may persist until the end of rehabilitation. Administration of the amino acid compositions disclosed in the instant application unexpectedly reduces pain and enhances the functional retrieval of hip joint function, as witnessed in the Results section.

Post-EHA patients show, in fact, muscle soreness, pain and weakness particularly after each session of physical therapy. A reduction in muscle soreness explains the reduction in the domain relative to pain observed in the study and found more pronounced in treated groups than in placebo ones.

Without wishing to be bound to any specific theory, it is reasonable to believe that supplementation with the amino acid compositions herein disclosed may influence the central nervous system contributing to reduce the domain of pain within HHS test, being the amino acids largely consumed by nervous system cells and being several of them precursors of neurotransmitters, and consequently a better retrieval of hip joint dysfunction is achieved.

According to some embodiments of the present disclosure, the amino acids isoleucine, leucine and valine are present in an amount expressed in moles percentage comprised in the range 50-70 mol % with respect to the total moles of the first active agent, preferably between 52-67 mol %.

In a further embodiment, the amino acids threonine and lysine are present in an amount expressed in moles percentage comprised in the range 20-30 mol % with respect to the total moles of the first active agent, preferably between 22-27 mol %.

In another embodiment, the amino acids histidine, phenylalanine, methionine and tryptophan are present in an amount expressed in moles percentage comprised in the range 5-15 mol % with respect to the total moles of the first active agent.

In a further embodiment, the amino acids tyrosine and cystine are present in an amount expressed in moles percentage comprised in the range 2-8 mol % with respect to the total moles of the first active agent.

In a still further embodiment, the first active agent comprises up to 70 mol % of isoleucine, leucine and valine, up to 50 mol % of threonine and lysine, up to 23 mol % of cystine, histidine, phenylalanine, methionine, tryptophan and tyrosine, wherein threonine and lysine are present together in a mole amount higher than the other essential amino acids with the exception of isoleucine, leucine and valine.

In a further embodiment, the first active agent consists of the amino acids leucine, isoleucine, valine, lysine, threonine, histidine, phenylalanine, methionine, tryptophan, tyrosine, and cystine.

In an embodiment, the composition herein disclosed may further comprise a second active agent comprising glutamine, serine and glycine.

In a further embodiment the amount of the second active agent expressed as moles percentage with respect to the total moles of the first active agent is comprised between 35-45 mol %, preferably 37-42 mol %, more preferably about 40 mol %.

According to an embodiment, when the amino acid composition comprises the first and second active agents, tyrosine is present in a mole amount higher than the mole amount of at least one of methionine, phenylalanine and cystine. In a preferred embodiment, tyrosine is present in a mole ratio with respect to methionine equal to or higher than 0.43 and/or tyrosine is present in a mole ratio with respect to phenylalanine equal to or higher than 0.85 and/or tyrosine is present in a mole ratio with respect to cystine equal to or higher than 0.49.

According to an embodiment, when the amino acid composition comprises the first and second active agents, histidine is present in a mole amount higher than the mole amount of threonine. In a preferred embodiment, histidine is present in a mole ratio with respect to threonine equal to or higher than 0.95.

According to an embodiment, when the amino acid composition comprises the first and second active agents, glutamine is present in a mole amount higher than the mole amount of at least one of isoleucine and valine. In a preferred embodiment, glutamine is present in a mole ratio with respect to isoleucine equal to or higher than 0.67 and/or glutamine is present in a mole ratio with respect to valine equal to or higher than 0.92.

According to an embodiment, when the amino acid composition comprises the first and second active agents, glycine is present in a mole amount higher than the mole amount of at least one of isoleucine and valine. In a preferred embodiment, glycine is present in a mole ratio with respect to isoleucine equal to or higher than 0.57 and/or glutamine is present in a mole ratio with respect to valine equal to or higher than 0.78.

According to an embodiment, when the amino acid composition comprises the first and second active agents, the non essential amino acids tyrosine, cystine, glutamine, serine and glycine are present in a mole amount lower than the mole amount of the essential amino acids contained in the composition; preferably tyrosine, cystine, glutamine, serine and glycine are present in an amount expressed in moles percentage comprised in the range 25-45 mol % with respect to the total moles of the composition, preferably between 30-40 mol %, more preferably about 34 mol %.

In a further embodiment, the second active agent consists of the amino acids glutamine, glycine and serine.

The presence of glutamine in the second active agent enhances the anabolic effect promoted by the essential amino acids contained in the first active agent, i.e. counteracting muscle proteolysis.

Furthermore, in particular, when preparing the compositions according to the instant disclosure, and specifically the active agents, the amino acids proline, alanine, and, above all, arginine are preferably avoided, given that they can be counterproductive or even harmful. Proline and alanine may, in fact, favour hypertension; arginine may interact negatively with drugs used in the treatment of pain.

The amino acids contained in the disclosed and claimed compositions can be replaced by respective pharmaceutically acceptable derivatives, namely salts.

In a preferred embodiment, the composition object of the instant description has a composition (expressed as a single dose sachet of 5 mg of amino acids) as disclosed in the following table 1.

TABLE 1

| Ingredient | mg/sachet | mole/sachet | mol/mol % | Range mol/mol % | Preferred range mol/mol % |
|---|---|---|---|---|---|
| L-Leucine | 1562.50 | 11.9175 | 31.97 | 15-50 | 25-37 |
| L-Isoleucine | 781.25 | 5.9587 | 15.98 | 5-30 | 10-20 |
| L-Valine | 781.25 | 6.6722 | 17.90 | 5-30 | 12-22 |
| L-Lysine | 812.50 | 5.5601 | 14.92 | 5-30 | 10-20 |
| L-Threonine | 437.50 | 3.6740 | 9.86 | 2-20 | 5-15 |
| L-Histidine | 187.50 | 1.2090 | 3.24 | 1-5 | 2-4 |
| L-Phenylalanine | 125.00 | 0.7572 | 2.03 | 0.5-6 | 1-4 |
| L-Tryptophan | 62.50 | 0.1225 | 0.33 | 0.1-0.5 | 0.2-0.4 |
| L-Methionine | 25.00 | 0.4191 | 1.12 | 0.5-2 | 0.75-1.5 |
| L-Tyrosine | 37.50 | 0.2071 | 0.56 | 0.1-1 | 0.2-0.7 |
| L-Cystine | 187.50 | 0.7805 | 2.09 | 0.5-5 | 1.5-2.5 |
| Total | 5000.00 | 37.28 | 100% | | |

From the data of Table 1 it is possible to calculate the molar ratios of the individual amino acids either with respect to the overall composition or with respect to each individual amino acid.

In a further preferred embodiment, the composition object of the instant description has a composition (expressed as a single dose sachet of 6651.00 mg of amino acids) as disclosed in the following table 2.

TABLE 2

| Ingredient | mg/sachet | mole/sachet | mol/mol % | Range mol/mol % | Preferred range mol/mol % |
|---|---|---|---|---|---|
| L-Leucine | 1500.00 | 11.4408 | 22.58 | 15-30 | 20-25 |
| L-Isoleucine | 450.00 | 3.4322 | 6.77 | 3-10 | 5-8 |
| L-Valine | 550.00 | 4.6972 | 9.27 | 5-15 | 7-12 |
| L-Lysine | 1000.00 | 6.8432 | 13.51 | 6-20 | 10-15 |
| L-Threonine | 246.00 | 2.0658 | 4.08 | 2-6 | 3-5 |
| L-Histidine | 336.00 | 2.1665 | 4.28 | 2-7 | 3-6 |
| L-Phenylalanine | 264.00 | 1.5991 | 3.16 | 1-5 | 2-4 |
| L-Tryptophan | 75.00 | 0.3674 | 0.73 | 0.3-1 | 0.5-0.9 |
| L-Methionine | 121.00 | 0.8114 | 1.60 | 0.5-3 | 1-2 |
| L-Tyrosine | 340.00 | 1.8775 | 3.71 | 1.5-6 | 3-4 |
| L-Cystine | 219.00 | 0.9116 | 1.80 | 0.9-2.7 | 1.5-2.0 |
| L-Glutamine | 750.00 | 5.1317 | 10.13 | 5-15 | 7-12 |
| L-Glycine | 450.00 | 5.9944 | 11.83 | 5-20 | 7-15 |
| L-Serine | 350.00 | 3.3305 | 6.57 | 3-10 | 5-9 |
| Total | 6651.00 | 50.67 | 100% | | |

From the data of Table 2 it is possible to calculate the molar ratios of the individual amino acids either with respect to the overall composition or with respect to each individual amino acid.

Supplementation of the herein disclosed and claimed amino acids compositions to patients, who underwent elective arthroplasty, both during post-exercise recovery and during the day, allows patients to continue rehabilitation, which on the contrary could be discontinued, thanks to the unexpected reduction of pain and muscle soreness.

Materials and Methods

Patients

Sixty-eight subjects at 17±1.12 days after elective hip arthoplasty (EHA) were recruited at admission to the rehabilitation center. The patients were selected on the basis of the type of surgical access they had had (lateral approach) in order to get a more uniformity in terms of recovery time. The causes for a EHA were: aseptic necrosis of the femoral head (5%), rheumatoid arthritis (1.6%), congenital hip dysplasia (1.6%), osteoarthritis (91.8%) of grade 3 and 4 diagnosed through preoperatory X-ray. Eight subjects were excluded for diabetes on insulin and/or oral hypoglycemic drugs (n=5), hyperthyroidism (n=1), chronic renal disease (n=2). Thus a total of 60 patients were studied.

On the second day after admission, the patients underwent the following procedures:

a) Anthropometric measurements: body weight (BW; kg) and height (m). Body mass index (BMI) was calculated as $kg/m^2$.

b) Biohumoral variables:

Routine Variables, including serum total protein (g/dL) and protein electrophoresis.

c) Clinical-functional status: this was measured using the Harris hip score (HHS) [1]. This is a test consisting of several domains relative to: pain, limp, support, distance walked, sitting, enter public transportation, stairs, putting shoes and socks on, absence of deformity and range of motion; the score range for each domain is shown in FIG. 2. The test gave outcome classification as poor (<70 scores), sufficient (70-79 scores), good (80-89 scores) or excellent (90-100 scores) [2].

After carrying out these procedures, the patients were randomly allocated to 14-d supplementation with the amino acid compositions herein disclosed (EAA) or a placebo (maltodextrin).

The treatment of 14 days was dictated by the rehabilitation center policy permitting patients to stay for at maximum 20 days.

Rehabilitation Protocol

This protocol aimed to restore the complete functional recovery of the altered body statics and the resumption of a normal pattern of walking. The rehabilitation program included 2 daily therapy sessions lasting 45 min each (morning and afternoon) with patients assisted by the same physical therapist.

The entire rehabilitation cycle encompasses 24 sessions. The rehabilitation program consisted of:
1) Passive mobilization of the hip with movements in triple flexion (hip, knee and ankle).
2) Stretching the adductor and flexor muscles of the operated limb.
3) Hip extension using isotonic contraction of the gluteus.
4) Isotonic contraction of the quadriceps muscles against a resistance of 1 kg.
5) Assisted gait training with the use of walking sticks and training for the stairs.
6) Maintenance of cardiorespiratory capacity.

The patients and physicians who evaluated on the subjects' functional status were blinded to the protocol. Within 2 days before patient discharge all procedures were repeated.

The local ethical scientific committee approved the protocol (#118 in the Maugeri Foundation Scientific Annals 2011, page 432) after the subjects gave their informed consent.

The Amino Acid Composition (EAA #1)

The experimental group (EAA group) received the composition herein disclosed in Table 4 (briefly named EAA #1) that provided 10 g of essential aminoacids/day (5 g in the morning+5 g in the afternoon diluted in about half a glass of water until patient discharge).

TABLE 4

| Main ingredients | | mg |
|---|---|---|
| Total amino acids including the following | | 5000 (in total) |
| L-Leucine | (131.17)* | 1562.50 |
| L-Isoleucine | (131.17)* | 781.25 |
| L-Valine | (117.15)* | 781.25 |
| L-Lysine | (146.19)* | 812.50 |
| L-Threonine | (119.12)* | 437.50 |
| L-Histidine | (155.16)* | 187.50 |
| L-Phenylalanine | (165.19)* | 125.00 |
| L-Methionine | (149.21)* | 62.50 |
| L-Tryptophan | (204.23)* | 25.00 |
| L-Tyrosine | (181.19)* | 37.50 |
| L-Cystine | (240.30)* | 187.50 |
| Excipients | | mg |
| Vitamin B6 | | 0.15 |
| Vitamin B1 | | 0.15 |

TABLE 4-continued

| Main ingredients | mg |
|---|---|
| Carbohydrates-Maltodextrins | 5454.10 |
| Banana flavour | 200.00 |
| Sodium citrate tribasic dehydrate | 150.00 |
| Aspartame powder | 30.00 |
| Acesulfame potassium | 17.50 |

*Molecular weight from "Amino Acid, Nucleic Acids & Related Compounds - Specification/General Tests", 8th Ed., Kyowa Hakko Kogyo Co., Ltd.

Statistical Analysis

Descriptive statistics were carried out for all recorded variables, reporting mean and standard deviations for quantitative variables and distribution frequencies for qualitative variables. Chi-squared test was used for categorical variables. Repeated measurement analysis of variance was used to assess any trend differences over time between patients on EAAs or placebo. Differences in plasma amino acids between patients and healthy controls and between the EAAs and placebo groups were analysed by unpaired Student t-test. Differences in the variables in the entire patient population observed at admission to and discharge from rehabilitation were tested by paired t-test. Statistical significance was set at p<0.05.

Results

Baseline Characteristics of Patient Population at Admission to Rehabilitation

At admission thirty-five percent of patients (n=21) were on antibiotic therapy for infection (mainly of urinary tract). Seventy percent (n=42) had received blood transfusions during their acute stage.

Functionally, the patients had severe reduction of hip function as indicated by their HHS test (40.78±2.70 scores). Within the test, the domain relative to pain showed that the patients had moderate pain (19.5±1.7 score).

After Randomization a) At Admission

After randomization, the EAA and placebo groups were similar for nutritional status, dietary intake, distribution in infection complications (40% in placebo, 30% in EAAs; n.s.). Compared to the placebo group, EAA subjects had lower serum transferrin (p=0.04) and circulating total proteins (p=0.04). Hip dysfunction was similar between the two patient groups (39.78±4.89 score in placebo vs 41.80±1.15 score in EAA group; n.s.). Within the test, all the domains including that relative to pain were similar between placebo and EAA subjects.

b) After 14-d Treatment

During rehabilitation, blood Hb and serum transferrin increased: +0.84±0.3 mg/dL in placebo vs +0.87±0.19 mg/dL in EAA group, interaction p=0.8 for Hb; +1.34±2.5 mg/dL in placebo vs+11.45±3.1 mg/dL in EAA group, interaction p=0.005 for transferrin. All the other biohumoral variables measured showed no significant changes both intra- and between the groups.

All patients improved hip dysfunction (from baseline 48.78±2.70 to 73.18±7.1 score; p<0.001) but EAA subjects improved more with respect to placebo group (from baseline 41.8±1.15 to 76.37±6.6 score vs 39.78±4.89 to 70.0±7.10 score) (interaction p=0.02); (FIG. 1).

Within the HHS test the EAA group showed a more marked reduction of the pain (from 20±0 to 39.2±5.59 score) than the placebo patients did (from 18.7±3.4 to 32.4±6.2 score) (interaction p=0.01).

Table 5 shows HHS and pain scores for the EAA and placebo groups.

TABLE 5

| | Placebo group | | EAA treated group | | |
|---|---|---|---|---|---|
| | admission | discharge | Admission | Discharge | Interaction P |
| Harris hip score | 39.78 ± 4.89 | 70.0 ± 7.10 | 41.8 ± 1.15 | 76.37 ± 6.6 | 0.02 |
| Pain score | 18.7 ± 3.4 | 32.4 ± 6.2 | 20 ± 0 | 39.2 ± 5.59 | 0.01 |

REFERENCES

1. Harris W H. Traumatic arthritis of the hip after dislocation and acetabular fractures: treatment by mold arthroplasty. An end-result study using a new method of result evaluation. J Bone Joint Surg Ann 1969; 51: 737-55.
2. Marchetti P, Binazzi R, Vaccari V, Girolami M, Morici F, Impallomeni C, et al. Long-term results with cementless Fitek (or Fitmore) cups. J Arthroplasty 2005; 20: 730-7.

The invention claimed is:

1. A composition for use in the treatment of pain in patients who underwent elective arthroplasty, the composition comprising at least a first active agent, wherein the first active agent comprises the amino acids leucine, isoleucine, valine, lysine, threonine, histidine, phenylalanine, methionine, tryptophan, tyrosine, and cystine,
    wherein the composition further comprises at least a second active agent, the second active agent comprising glutamine, serine and glycine,
    wherein the composition is free of arginine, proline, alanine,
    glycine is present in a mole amount higher than the mole amount of at least one of isoleucine and valine.

2. The composition for use according to claim 1, wherein the amino acids isoleucine, leucine and valine are present in an amount expressed in moles percentage with respect to the total mole amount of the first active agent comprised in the range 50-70 mol % with respect to the total moles of the first active agent.

3. The composition for use according to claim 1, wherein the amino acids threonine and lysine are present in an amount expressed in moles percentage with respect to the total mole amount of the first active agent comprised in the range 20-30 mol % with respect to the total moles of the first active agent.

4. The composition for use according to claim 1, wherein the amino acids histidine, phenylalanine, methionine and tryptophan are present in an amount expressed in moles percentage with respect to the total mole amount of the first active agent comprised in the range 5-15 mol % with respect to the total moles of the first active agent.

5. The composition for use according to claim 1, wherein the amino acids tyrosine and cystine are present in an amount expressed in moles percentage with respect to the total mole amount of the first active agent comprised in the range 2-8 mol % with respect to the total moles of the first active agent.

6. The composition for use according to claim 1, wherein the amount of the second active agent expressed as moles percentage with respect to the total moles of the first active agent is comprised between 35-45 mol %.

7. The composition for use according to claim 1, wherein tyrosine is present in a mole amount higher than the mole amount of at least one of methionine, phenylalanine and cystine.

8. The composition for use according to claim 1, wherein histidine is present in a mole amount higher than the mole amount of threonine.

9. The composition for use according to claim 1, wherein glutamine is present in a mole amount higher than the mole amount of at least one of isoleucine and valine.

10. The composition for use according to claim 1, tyrosine, cystine, glutamine, serine and glycine are present in an amount expressed in moles percentage with respect to the total moles of the composition comprised in the range 25-45 mol %.

11. The composition for use according to claim 1, wherein the composition comprises at least one excipient.

12. The composition for use according to claim 11, wherein the at least one excipient is selected from: proteins, vitamins, carbohydrates, natural and/or artificial sweeteners, flavouring substances.

* * * * *